(12) United States Patent
Sommer et al.

(10) Patent No.: US 11,579,230 B2
(45) Date of Patent: Feb. 14, 2023

(54) MULTI-STATE MAGNETIC RESONANCE FINGERPRINTING

(71) Applicant: KONINKLIJKE PHILIPS N.V., Eindhoven (NL)

(72) Inventors: Karsten Sommer, Hamburg (DE); Mariya Ivanova Doneva, Hamburg (DE); Thomas Erik Amthor, Hamburg (DE); Peter Koken, Hamburg (DE); Jan Jakob Meineke, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 869 days.

(21) Appl. No.: 16/468,849

(22) PCT Filed: Dec. 6, 2017

(86) PCT No.: PCT/EP2017/081601
§ 371 (c)(1),
(2) Date: Jun. 12, 2019

(87) PCT Pub. No.: WO2018/108643
PCT Pub. Date: Jun. 21, 2018

(65) Prior Publication Data
US 2020/0096589 A1    Mar. 26, 2020

(30) Foreign Application Priority Data
Dec. 15, 2016 (EP) .................... 16204246

(51) Int. Cl.
*G01R 33/561* (2006.01)
*G01R 33/50* (2006.01)
(Continued)

(52) U.S. Cl.
CPC ......... *G01R 33/5613* (2013.01); *G01R 33/50* (2013.01); *G01R 33/543* (2013.01);
(Continued)

(58) Field of Classification Search
CPC .. G01R 33/5613; G01R 33/50; G01R 33/543; G01R 33/5602; G16H 30/20;
(Continued)

(56) References Cited

U.S. PATENT DOCUMENTS

2009/0322331 A1* 12/2009 Buracas ............. G01R 33/5614
                                                          324/309
2013/0265047 A1  10/2013 Griswold et al.
(Continued)

OTHER PUBLICATIONS

D. Ma et al., "Magnetic Resonance Fingerprinting", Nature 495, 187 (2013).
(Continued)

*Primary Examiner* — Bobbak Safaipour
*Assistant Examiner* — Duy Tran (57) ABSTRACT

The invention provides for a magnetic resonance imaging system (100) for acquiring magnetic resonance data (142) from a subject (118) within a measurement zone (108). The magnetic resonance imaging system (100) comprises: a processor (130) for controlling the magnetic resonance imaging system (100) and a memory (136) storing machine executable instructions (150, 152, 154), pulse sequence commands (140) and a dictionary (144). The pulse sequence commands (140) are configured for controlling the magnetic resonance imaging system (100) to acquire the magnetic resonance data (142) of multiple steady state free precession (SSFP) states per repetition time. The pulse sequence commands (140) are further configured for controlling the magnetic resonance imaging system (100) to acquire the magnetic resonance data (142) of the multiple steady state free precession (SSFP) states according to a magnetic resonance fingerprinting protocol. The dictionary (144) comprises a plurality of tissue parameter sets. Each tissue parameter set is assigned with signal evolution data pre-calculated for multiple SSFP states.

15 Claims, 5 Drawing Sheets

(51) Int. Cl.
| | |
|---|---|
| *G01R 33/56* | (2006.01) |
| *G01R 33/54* | (2006.01) |
| *G06T 11/00* | (2006.01) |
| *G06T 7/00* | (2017.01) |
| *G06K 9/00* | (2022.01) |
| *G16H 30/20* | (2018.01) |
| *G06V 20/64* | (2022.01) |

(52) U.S. Cl.
CPC ........ *G01R 33/5602* (2013.01); *G06T 7/0016* (2013.01); *G06T 11/005* (2013.01); *G06V 20/653* (2022.01); *G16H 30/20* (2018.01); *G06T 2207/10088* (2013.01); *G06T 2207/30096* (2013.01); *G06V 2201/03* (2022.01)

(58) Field of Classification Search
CPC .............. G06V 20/653; G06V 2201/03; G06T 7/0016; G06T 11/005; G06T 2207/10088; G06T 2207/30096
See application file for complete search history.

(56) References Cited

U.S. PATENT DOCUMENTS

| | | | |
|---|---|---|---|
| 2013/0271132 A1 | 10/2013 | Griswold | |
| 2013/0314086 A1* | 11/2013 | Li | G01R 33/5613 324/309 |
| 2014/0002076 A1* | 1/2014 | Warntjes | G01R 33/50 324/309 |
| 2014/0218027 A1 | 8/2014 | Fautz | |
| 2014/0292325 A1* | 10/2014 | Heule | G01R 33/448 324/309 |
| 2015/0301138 A1* | 10/2015 | Griswold | G01R 33/56366 324/309 |
| 2015/0346300 A1 | 12/2015 | Setsompop et al. | |
| 2016/0116559 A1 | 4/2016 | Cohen | |
| 2016/0282437 A1* | 9/2016 | Park | G01R 33/5614 |

OTHER PUBLICATIONS

Y. Jiang et al., "MR Fingerprinting Using Fast Imaging with Steady State Percission (FISP) with Spiral Readout" Magn Reson Med 74:1621-1631 (2014).

E.Y. Pierre et al., "Multiscale Reconstruction for Magnetic Resonance Fingerprinting" Magn Reson Med, DOI: 10.1002/mrm.25776 (2015).

K. Sommer et al., "Towards Judging the Encoding Capability of Magnetic Resonance Fingerprinting Sequences" Proc Intl Soc Mag Reson Med 24, No. 429 (2016).

B. Zhao et al., "Towards Optimized Experiment Design for Magnetic Resonance Fingerprinting" Proc Intl Soc Mag Reson Med 24, No. 2835 (2016).

C.T. Mizumoto, E. Yoshitome, "Multiple Echo SSFP Sequences" Magn Reson Med 18:244-250 (1991).

B. Madore et al., "Quantitative MR Imaging Method" Proc Intl Soc Mag Reson Med 22, No. 0336 (2014).

International Search Report dated Feb. 22, 2018.

Jakob Asslander et al., "Pseudo Steady-State Free Precession for MR-Fingerprinting" Magnetic Resonance in Medicine, vol. 77, No. 3, p. 1151-1161 Mar. 2017.

Yun Jiang et al MR Fingerprinting Using Fast Imaging with Steady State Precession (FISP) with Spiral Readout Magnetic Resonance in Medicine 74:1621-1631 (2015).

Tony Stocker MR Parameter Quantification with Magnetization-Prepared Double Echo Steady-State (MP-DESS); Magnetic Resonance in Medicine 72:103-111 (2014).

Simone Coppo et al: "Overview of Magnetic Resonance Fingerprinting", Feb. 1, 2016 (Feb. 1, 2016), XP055380755, Retrieved from the Internet: URL:http://clinical-mri.com/wp-content/uploads/2016/04/Gulani_MRF_MAGNETOM_Flash_ISM_RM_2016.pdf (2016).

Kiaran Mcgee et al: "Pulse Sequence Basics" "Mayo Clinic Guide to Cardiac Magnetic Resonance Imaging", May 28, 2015 (May 28, 2015), Oxford University Press, XP055381312, pp. 45-47.

Edelstein WA et al: "MRI:Time Is Dose-and Money and Versatility", Journal of the American College of Radiology, Elsevier, Amsterdam, NL, vol. 7, No. 8, Aug. 1, 2010 (Aug. 1, 2010),pp. 650-652, XP027186358, ISSN:1546-1440.

Mizumoto et al.: "Multiple Echo SSFP Sequences",Magnetic Resonance in Medicine, vol. 18, 1991, pp. 244-250 (1991).

Scheffler: "A Pictorial Description of Steady-States in Rapid Magnetic Resonance Imaging", Concepts in Magnetic Resonance,vol. 11, No. 5, 1999, pp. 291-304.

Mariya Doneva et al: "Compressed Sensing in Quantitative MRI" In: "MRI Physics, Image Reconstruction, and Analysis",Jan. 1, 2015 (Jan. 1, 2015), CRC Press,XP055380710,pp. 51-71.

Wiegel, M "Extended Phase Graphs: Dephasing, RF Pulses and Echos . . . " Journal of Magnetic Resonance Imaging, vol. 41, p. 266-295 (2015).

Heule et al "Triple Echo Steady-State (TESS) Relaxometry" Magnetic Resonance in Med. vol. 71, pp. 230-237 (2014).

* cited by examiner

MULTI-STATE MAGNETIC RESONANCE FINGERPRINTING

CROSS REFERENCE TO RELATED APPLICATIONS

This application is a U.S. national phase application of International Application No. PCT/EP2017/081601 filed on Dec. 6, 2017, which claims the benefit of EP Application Ser. No. 16204246.9 filed on Dec. 15, 2016 and is incorporated herein by reference.

FIELD OF THE INVENTION

The invention relates to magnetic resonance imaging, in particular to magnetic resonance fingerprinting.

BACKGROUND OF THE INVENTION

Magnetic Resonance fingerprinting (MRF) is a technique where a number of RF pulses, distributed in time, are applied such that they cause signals from different types of tissues to have a unique contribution to the measured Magnetic Resonance (MR) signal. A limited dictionary of pre-calculated signal contributions from a set or fixed number of tissue parameters identifying a particular type or composition of tissues is compared to the measured MR signals and within a single voxel the parameters identifying the type or composition of tissues causing the measured MR signal can be determined. For example, if it is known that a voxel only contains water, fat, and muscle tissue the contribution of tissue parameters identifying these three materials and their compositions need only be considered and only a few RF pulses are needed to accurately determine the parameters of the composition of tissues of the voxel.

The magnetic resonance fingerprinting technique was introduced in the journal article Ma et al., "Magnetic Resonance Fingerprinting", Nature, vol. 495, pp. 187 to 193 (2013). The magnetic fingerprinting technique is also described in United States patent applications US 2013/0271132 A1 and US 2013/0265047 A1.

SUMMARY OF THE INVENTION

The invention provides for a magnetic resonance imaging system, a computer program product, and a method in the independent claims. Embodiments are given in the dependent claims.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three-dimensional visualization of anatomic data contained within the magnetic resonance imaging data. This visualization can be performed using a computer.

In case of conventional parametric mapping approaches, e.g. conventional T1 and T2 mapping techniques, several fully sampled images are acquired one after the other with different inversion time for T1 mapping or different echo time for T2 mapping. A relaxation time for the T1 mapped data and a decay time for the T2 mapped data are determined by applying an exponential fitting using the multiple values of each voxel resulting from the variation of T1 and T2, respectively.

This conventional quantitative MRI approach, however, has the drawback of being highly time consuming, since only one parameter is measured at a time. Magnetic resonance data for several images are acquired with one specific acquisition parameter being varied for each image while all other acquisition parameters are kept constant. The obtained MRI data is subsequently fitted with a mathematical model to estimate the one acquisition parameter of interest, like e.g. the relaxation time (T1) or the time of signal decay (T2). In order to obtain information regarding more than one acquisition parameter, the aforementioned process has to be repeated for each parameter of interest. However, for clinical adoption of MRI techniques, there is a major need for rapid and accurate quantification.

The Nature article by Ma et al. introduces the basic idea of magnetic resonance fingerprinting and terminology which is used to describe this technique such as the dictionary, which is understood to refer to a magnetic resonance fingerprinting dictionary.

In magnetic resonance fingerprinting, tissue parameters are acquired based on a signal evolution for voxels. Acquisition parameters for acquiring the signal are varied, the resulting signal evolution curve also referred to as a "fingerprint" of the type or composition of tissues causing the measured MR signal is recorded. For example, a pattern recognition algorithm is used to find a dictionary entry that best represents the acquired signal evolution of each voxel. Each fingerprint in the dictionary points to the MR related identification features of the associated tissue.

In one aspect, the invention provides for a magnetic resonance imaging system for acquiring magnetic resonance data from a subject within a measurement zone. The magnetic resonance imaging system comprises a processor for controlling the magnetic resonance imaging system. The magnetic resonance imaging system further comprises a memory storing machine-executable instructions. The memory is further for storing pulse sequence commands and a dictionary. The pulse sequence commands are configured for controlling the magnetic resonance imaging system to acquire magnetic resonance data of multiple steady state free precession (SSFP) states. The pulse sequence commands are further configured for controlling the magnetic resonance imaging system to acquire the magnetic resonance data of the multiple steady state free precession (SSFP) states according to a magnetic resonance fingerprinting protocol.

The dictionary comprises a plurality of tissue parameter sets. Each of the tissue parameter sets is assigned with signal evolution data pre-calculated for multiple SSFP states.

An execution of the machine executable instructions causes the processor to acquire the magnetic resonance data of the multiple SSFP states for a plurality of voxels by controlling the magnetic resonance imaging system with the pulse sequence commands according to the magnetic resonance fingerprinting protocol. Further, a tissue parameter map is reconstructed for the acquired multiple SSFP state magnetic resonance data. For each voxel, the pre-calculated signal evolution data provided by the dictionary which best matches the acquired multiple SSFP state magnetic resonance data is identified and the tissue parameter set of the best matching pre-calculated resonance signal evolution data is assigned to the respective voxel.

According to embodiments of the invention the pulse sequence commands are configured for controlling the magnetic resonance imaging system to acquire magnetic resonance data of multiple steady state free precession (SSFP) states per repetition time and the processor is caused to acquire the magnetic resonance data of the multiple SSFP states per repetition time for a plurality of voxels by controlling the magnetic resonance imaging system with the pulse sequence commands according to the magnetic resonance fingerprinting protocol.

SSFP states are for example described in the journal article Scheffler, "A Pictorial Description of Steady-States in Rapid Magnetic Resonance Imaging", Concepts in Magnetic Resonance, vol. 11(5), pp. 291 to 304 (1999). Also, Wiegel, M, "Extended phase graphs: Dephasing, RF pulses, and Echos—Pure and Simple, Journal of magnetic resonance imaging, vol. 41 pp. 266-295 (2015) gives an explanation of the concept.

The acquisition of multiple SSFP states after each excitation pulse may be realized by extending and expanding the application of the readout gradient generated according to the pulse sequence commands. Magnetic resonance data of the different SSFP states may be acquired successively, i.e. at different points of time during the same repetition. By suitably tuning the readout gradient, the point of time at which the magnetic resonance data of each of the different SSFP states is acquired. A controlling of the number of multiple SSFP states by extending and expanding the application of a readout gradient is e.g. described in general in the journal article Mizumoto et al., "Multiple Echo SSFP Sequences", Magnetic resonance in medicine, vol. 18, pp. 244 to 250 (1991). Such a pulse sequence may further be modified by varying the sequence parameters such as e.g. FA, RF phase, and TR throughout the acquisition. Heule et al., "Triple Echo Steady-State (TESS) Relaxometry" Magnetic resonance in medicine, vol. 71 pp 230-237 (2014) shows how a pulse sequence may look like to acquire multiple SSFP states. By acquiring multiple SSFP states after each excitation pulse, considerably more information may be obtained in the same measurement time compared to known MRF approaches. Hence, embodiments of the invention may improve efficiency, accuracy, and/or precision.

Magnetic Resonance Fingerprinting (MRF) may provide for fast and accurate quantification of tissue parameters such as T1 and T2. It relies on the continuous variation of sequence parameters such as the flip angle (FA) during the acquisition, thereby creating signal evolution curves that are assumed to be characteristic of the underlying tissue. A subsequent matching of the acquired signals to a pre-calculated database of possible signal evolution curve, i.e. a dictionary entry, may then yield the desired tissue parameters.

MRF may provide simultaneous measurements of multiple acquisition parameters, like e.g. T1, T2, relative spin density ($M_0$), $B_0$ inhomogeneity, etc., using a single, time-efficient acquisition.

A plurality of acquisition parameters is varied deliberately e.g. in a pseudo-random fashion such that each tissue or combination of tissues generates a unique signal evolution. In addition, signal evolution data may be simulated from first principles using different physical models for a wide variety of tissue parameter combinations. This simulated signal evolution data is collected in the dictionary. After the data acquisition, a pattern recognition algorithm may be applied to find for each signal evolution of each voxel the dictionary entry which best represents the respective signal evolution. Then, for each voxel the parameters that were used to simulate the best matching dictionary entry identified for the signal evolution acquired from the respective voxel are assigned to the voxel. The acquired signal evolution is unique for each tissue and can be seen as the collected fingerprint that has to be identified. Each fingerprint in the dictionary points to the MR related identification features of the associated tissue like e.g. T1, T2, $M_0$, $B_0$, diffusion, etc.

For commonly used magnetic resonance fingerprinting sequences, the encoding capability is usually much higher for T1 than T2. Consequently, the minimum length of an employed flip angle (FA) pattern, and therefore of the entire measurement, is mainly determined by the accuracy of the T2 estimates. For most MRF sequences, T2 estimates require a rather long signal evolution time to obtain accurate T2 estimates, so that relatively long FA patterns have to be employed.

Embodiments may have advantage of reducing the required acquisition time. This may be achieved by increasing the encoding capabilities for T2 due to acquiring multiple SSFP states per repetition time. Such a higher encoding capability for T2 may drastically reduce the required acquisition time.

According to embodiments, the pre-calculated signal evolution data for each of the tissue parameter sets comprises data of a plurality of pre-calculated signal evolution curves. Each of the pre-calculated signal evolution curves is assigned to one SSFP state of the multiple SSFP states and characterizes a signal evolution of the respective SSFP state. The identification of the pre-calculated signal evolution data best matching the acquired multiple SSFP state magnetic resonance data further comprises determining matching factors for each comparison of acquired signal evolution curves and pre-calculated signal evolution curves which are assigned to the same SSFP state and using the matching factors for identifying the best matching pre-calculated signal evolution data.

Embodiments may have the beneficial effect that the tissue parameter set which best describes the type or combination of tissue types causing the acquired multiple SSFP state magnetic resonance data may efficiently be identified. Since matching for multiple pre-calculated signal evolution curves is carried out for each dictionary entry, i.e. tissue parameter set, the probability of a mismatch due to measurement errors may be reduced. This may result in an improved robustness against measurement errors compared to standard MRF methods, thus allowing a reduction of the total acquisition time by shortening variation pattern employed according to the MRF protocol.

According to embodiments, the determining of matching factors further comprises calculating an average matching factor for the pre-calculated signal evolution data of each tissue parameter set. The pre-calculated signal evolution data with the best average matching factor is identified as being the pre-calculated signal evolution data best matching the acquired multiple SSFP state magnetic resonance data.

Embodiments may have the beneficial effect of efficiently taking into account multiple matching procedures for multiple pre-calculated signal evolution curves.

According to embodiments, the matching of the acquired multiple SSFP state magnetic resonance data with the pre-calculated signal evolution data comprises determining an inner product between the normalized acquired signal evolution curves and the normalized signal evolution curves which are assigned to the same SSFP state. The best average match is given by the highest average inner product of the inner products.

Embodiments may have the beneficial effect of providing a robust operation by using the inner product for identifying the best matching pre-calculated signal evolution data. An analysis using inner products is able to correctly classify tissue parameter sets, i.e. tissues underlying the acquired multiple SSFP state magnetic resonance data, even in case of low SNR due to undersampling or even in the presence of a limited amount of motion artifacts.

For an analysis of the acquired multi-state SSFP signals, a specific dictionary may be calculated that contains for each tissue parameter set comprised the characteristic signal evolution data of all employed SSFP states for the employed MRF sequences. Each tissue parameter set, like e.g. a T1/T2-combination, comprised by the dictionary may be assigned with multiple different SSFP signal curves. The acquired signals, i.e. acquired signal evolution curves, may be matched to each of the signal curves in the dictionary which are assigned to the same SSFP state. For n different SSFP states $F_i$ comprised by the normalized acquired multiple SSFP signal, for each normalized dictionary entry, i.e. tissue parameter set, n different inner products $\theta_i$ (also referred to as vector dot-products) may be calculated, i.e. one inner product $\theta_i$ for each SSFP states $F_i$ with i indicating the order of the SSFP state. The normalization may for example be such that each of the respective quantities has the same sum squared magnitude. The most suitable tissue parameter set, e.g. T1/T2-combination, may be identified as the one that yields the highest average inner product, i.e. $\bar{\theta}=1/n\Sigma_i\theta_i$. Since multiple matching procedures are carried out for each dictionary entry, the probability of a mismatch due to measurement errors such as noise may be substantially reduced. Consequently, the multi-state SSFP MRF approach described herein may exhibit an improved robustness against measurement errors compared to standard MRF approaches. This may allow for a reduction of the total acquisition time by shortening the variation pattern employed, like e.g. a FA pattern.

According to embodiments, the identification of the pre-calculated signal evolution data best matching the acquired multiple SSFP state magnetic resonance data further comprises weighting the results of the comparing of the acquired multiple SSFP state magnetic resonance data with the individual pre-calculated signal evolution curves using weighting factors. Embodiments may have the beneficial effect of taking into account different quality and/or significance of individual pre-calculated signal evolution curves, i.e. SSFP states.

According to embodiments, the results of the comparing of pre-calculated signal evolution curves assigned to higher-order SSFP states are assigned with smaller weighting factors than the results of the comparing with signal evolutions assigned to lower-order SSFP states.

According to embodiments, knowledge of the typical signal-to-noise ratios (SNRs) of the different SSFP states may incorporated in the matching process, i.e. instead of using the arithmetic mean to identify the most suitable tissue parameter set, a weighting of the different inner products may be introduced:

$$\bar{\theta} = \frac{1}{n}\sum_i w_i\theta_i,$$

where $w_i$ is the weighting factor of the inner product $\theta_i$ of SSFP states $F_i$. For example, higher-order SSFP states $F_i$ with $|i|>1$, like e.g. i=2, 3, 4, or higher, may have a lower SNR and may thus, in order to improve the total SNR, be weighted with a smaller weighting factor such that their SNR contribution to the total SNR is reduced. Higher-order $F_i$ have a strongly reduced, i.e. exponentially decreased as a function of i, intensity compared to the most intense $F_0$ state. Since noise in magnetic resonance data acquisition being independent of the order SSFP state, the SNR for high-order $F_i$ is drastically, i.e. exponentially, reduced compared to lower-order $F_i$.

According to embodiments, the acquired multiple SSFP state magnetic resonance data comprises magnetic resonance data of three or more SSFP states, e.g. five, seven, nine, etc. According to embodiments, the acquired multiple SSFP state magnetic resonance data comprises magnetic resonance data of the central SSFP states.

According to embodiments, the acquired multiple SSFP state magnetic resonance data comprises magnetic resonance data of the following SSFP states: $F_{-2}$, $F_{-1}$, $F_0$, $F_1$, and $F_2$.

Embodiments may have the beneficial effect of providing a suitable basis for an efficient and effective data analysis. The intensity of the low-order SSFP states $F_i$ with $|i|<1$ is higher compared to the high order SSFP states $F_i|i|>1$ for which the intensity exponentially decreases with n. However, the higher-order SSFP states, i.e. $F_{-2}$ and $F_2$ exhibit a more pronounced T2 dependence. Thus, taking into account higher-order SSFP states may increase the accuracy of the T2 estimates allowing to reduce the acquisition time.

According to embodiments, the acquiring of the multiple SSFP state magnetic resonance data according to the magnetic resonance fingerprinting protocol comprises varying one or more of the following parameters during the acquisition of the multiple SSFP state magnetic resonance data: an absolute value of a flip angle, a radiofrequency phase, a gradient field, an echo time, and the repetition time. According to embodiments, the parameters are varied independently. For example, one or more pseudo-random patterns may be used for varying the parameters. According to further embodiments other patterns may be used.

Varying the absolute value of the radiofrequency excitation angle, also referred to as flip angle or FA, the radiofrequency phase, the gradient field, and the repetition time (TR), throughout the acquisition, uncorrelated evolution signals for different tissue parameters and different SSFP states may be acquired. These uncorrelated evolution signals are unique fingerprints that may be used to recognize the underlying type or combination of tissue types.

Varying echo times for the different SSFP states may be realized by modifying the readout gradient throughout the scan to introduce an additional T2 weighting. This variation is accounted for in the calculation of the dictionary.

According to embodiments, execution of the machine executable instructions further causes the processor to pre-calculate the signal evolution data of the dictionary, wherein the signal evolution data for the multiple SSFP states is pre-calculated for each tissue parameter set of the dictionary, and to store the pre-calculated signal evolution data in store the pre-calculated signal evolution data in the memory. For example, the dictionary may be calculated by solving the Bloch equation or by performing an extended phase graph calculation.

According to embodiments, the pre-calculation of the signal evolution data comprises modeling for each one of the multiple SSFP states signal evolution data using variations of one or more of the following parameters: the absolute value of the flip angle, the radiofrequency phase, the gradient field, the echo time, and the repetition time.

According to embodiments, the dictionary may be generated by modeling each of the pre-determined tissues for which the dictionary comprises tissue parameter sets using an extended phase graph formulation. The extended phase graph formulation is for example described in Weigel, "Extended phase graphs: Dephasing, RF pulses, and echoes—pure and simple", Journal of Magnetic Resonance Imaging, vol. 41, pp. 266 to 295, (2015) and is also described in Scheffler, "A Pictorial Description of Steady-States in Rapid Magnetic Resonance Imaging", Concepts in Magnetic Resonance, vol. 11(5), pp. 291 to 304 (1999).

According to embodiments, one or more magnetic resonance images are reconstructed using the tissue parameter map.

Embodiments may have the beneficial effect of allowing to reconstruct magnetic resonance images of the subject in the measurement zone representing different tissue parameters, i.e. acquisition parameters, like e.g. T1 weighted images or T2 weighted images. In T1 weighted imaging T2 relaxation effects are minimized. Tissues with high fat content, like e.g. white matter, appear bright and compartments filled with water, like e.g. cerebral spinal fluid (CSF), appear dark. Such a contrast selection may be beneficial for representing anatomy. In T2 weighted imaging T1 relaxation effects are minimized. Compartments filled with water, like e.g. CSF compartments, appear bright, while tissues with high fat content, like e.g. white matter, appear dark. T2 weighted images may be beneficial for pathology, since e.g. most lesions are associated with an increase in water content.

In another aspect, the invention provides for a computer program product comprising machine-executable instructions for execution by a processor controlling a magnetic resonance imaging system to acquire magnetic resonance data from a subject within a measurement zone. The execution of the machine executable instructions causes the processor to acquire magnetic resonance data of multiple SSFP states per repetition time for a plurality of voxels according to a magnetic resonance fingerprinting protocol by controlling the magnetic resonance imaging system with pulse sequence commands. The pulse sequence commands are configured for controlling the magnetic resonance imaging system to acquire the magnetic resonance data of the multiple SSFP states per repetition according to the magnetic resonance fingerprinting protocol.

The execution of the machine executable instructions further causes the processor to reconstruct a tissue parameter map for the acquired multiple SSFP state magnetic resonance data. The reconstruction comprises for each voxel identifying pre-calculated signal evolution data provided by dictionary which best matches the acquired multiple SSFP state magnetic resonance data and assigning the tissue parameter set of the best matching pre-calculated resonance signal evolution data to the respective voxel. The dictionary comprises a plurality of tissue parameter sets, each tissue parameter set being assigned with signal evolution data pre-calculated for multiple SSFP states.

The computer program product may comprising machine-executable instructions for execution by a processor which are configured for controlling a magnetic resonance imaging system to implement any of the aforementioned embodiments.

In another aspect, the invention further provides for a method of operating the magnetic resonance imaging system for acquiring magnetic resonance data from a subject within a measurement zone. The method comprises acquiring magnetic resonance data of multiple SSFP states per repetition time for a plurality of voxels according to a magnetic resonance fingerprinting protocol by controlling the magnetic resonance imaging system with pulse sequence commands. The pulse sequence commands are configured for controlling the magnetic resonance imaging system to acquire the magnetic resonance data of the multiple SSFP states per repetition according to the magnetic resonance fingerprinting protocol.

The method further comprises reconstructing a tissue parameter map for the acquired multiple SSFP state magnetic resonance data. The reconstruction comprises for each voxel identifying pre-calculated signal evolution data provided by dictionary which best matches the acquired multiple SSFP state magnetic resonance data and assigning the tissue parameter set of the best matching resonance pre-calculated signal evolution data to the respective voxel. The dictionary comprises a plurality of tissue parameter sets, each tissue parameter set being assigned with signal evolution data pre-calculated for multiple SSFP states.

The method may be configured for operating the magnetic resonance imaging system to implement any of the aforementioned embodiments.

The aforementioned embodiments of the invention may thus provide:
  An MR fingerprinting sequence that acquires multiple SSFP states per TR;
  A method to calculate a dictionary that contains characteristic signal evolution data of all acquired SSFP states;
  A method to perform the matching to the multiple-state dictionary, i.e. to reconstruct tissue parameter maps.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments, computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
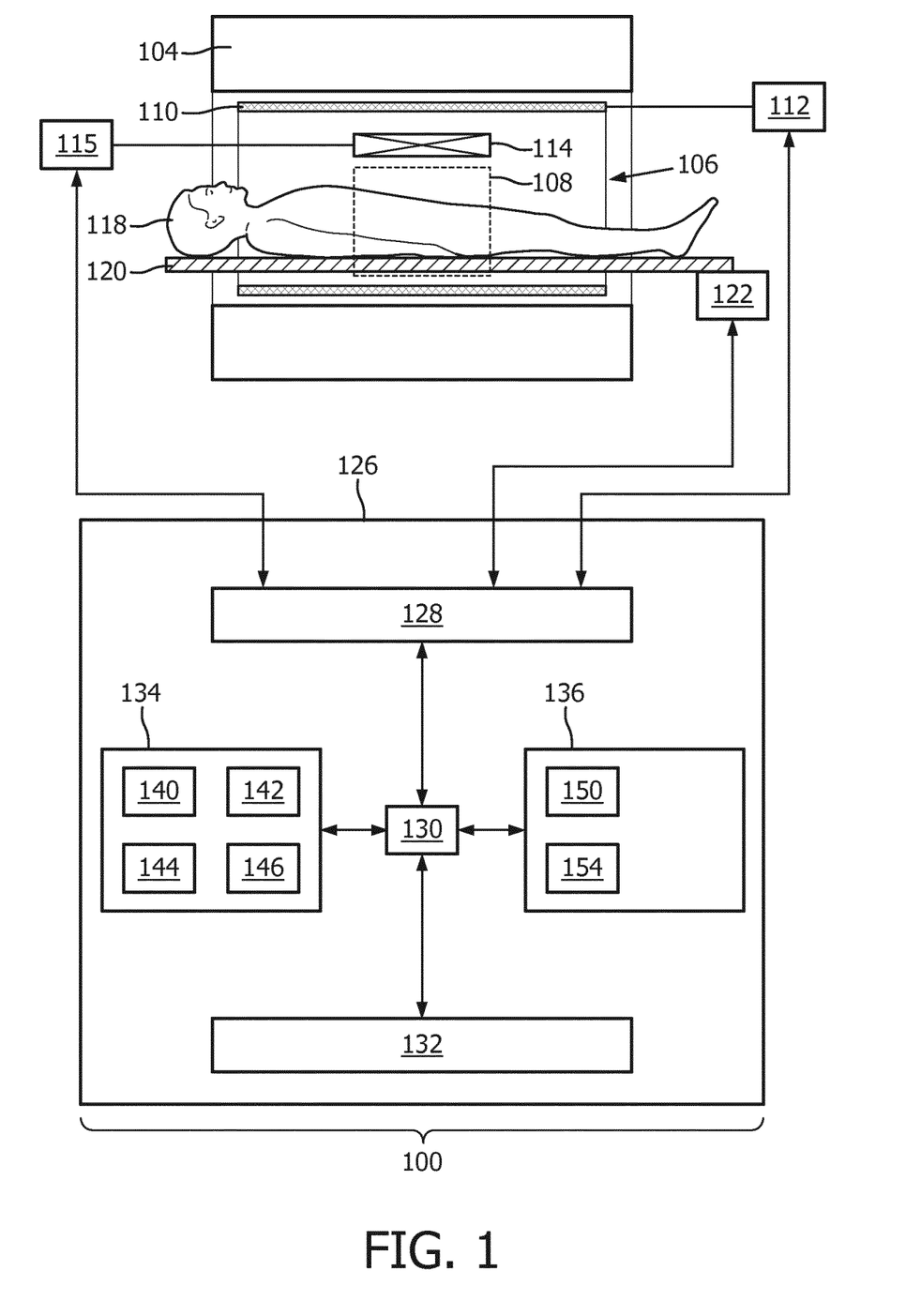
FIG. 1 illustrates a schematic diagram of an exemplary magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise, the transceiver 116 may also represent a separate transmitter and receivers. The radio-frequency coil 114 may also have multiple receive/transmit elements and the radio frequency transceiver 116 may have multiple receive/transmit channels.

The subject support 120 is attached to an optional actuator 122 that is able to move the subject support and the subject 118 through the imaging zone 108. In this way, a larger portion of the subject 118 or the entire subject 118 can be imaged. The transceiver 116, the magnetic field gradient coil power supply 112 and the actuator 122 are all see as being connected to a hardware interface 128 of computer system 126. The computer storage 134 is shown as containing pulse sequence commands 140 for performing a magnetic resonance fingerprinting technique.

The pulse sequence commands 140 cause the magnetic resonance system to acquire the magnetic resonance data according to a magnetic resonance fingerprinting technique. The pulse sequence commands may specify a pulse sequence for repeatedly acquiring magnetic resonance data 142 with varying the acquisition parameters. The pulse sequence may comprise a plurality of radio frequency pulses, e.g. 250 RF pulses to 1000 RF pulses, each corresponding to a data acquisition step, i.e. a sequence step, with a repetition time assigned to the step. Acquisition parameters defined by the pulse sequence may vary from acquisition step to acquisition step, i.e. for each repetition time. Thus, the magnetic resonance data may be acquired using different acquisition parameters at each sequence step. Furthermore, multiple SSFP states may be acquired per repetition time, i.e. per sequence step. Such an acquisition of multiple SSFP states per repetition time may be realized by extending and expanding the application of a readout gradient after each radio frequency pulse. For this purpose, the pulse sequence commands 140 may specify the application of gradient magnetic fields in at least one direction by controlling the supplied current to the set of gradient coils 110. Thus, for each of the multiple SSFP states magnetic resonance data 142 may be acquired at each sequence step, wherein the acquisition parameters vary from acquisition step to acquisition step. Since during each repetition time magnetic resonance data 142 of different SSFP states may be acquired at different points of time, the magnetic resonance data 142 of different SSFP states may be deinterleaved or disentangle, resulting in a multitude of different signal evolution curves, each acquired for an individual SSFP state. For example, one or more of the following acquisition parameters of the pulse sequence may be varied from acquisition step to acquisition step: an absolute value of a flip angle, a radiofrequency phase, a gradient field, an echo time, and the repetition time. Thus, for example the distribution of radio frequency pulses provided by the pulse sequence may cause magnetic spins to rotate to a distribution of flip angles. Acquiring magnetic resonance data 142 of multiple SSFP states per repetition time, i.e. during the same data acquisition operation, may allow significantly reducing the acquisition time which is required for acquiring sufficient magnetic resonance data 142 for reconstructing magnetic resonance images of a desired quality. In particular, taking into account higher-order SSFP states, which have a pronounced T2 dependence may result in a higher encoding capability for T2. Hence, the required acquisition time for acquiring sufficient magnetic resonance data 142 may in particular be reduce in view of T2 compared to known approaches.

The computer storage 134 is further shown as containing magnetic resonance data 142 that was acquired using the pulse sequence commands 140 to control the magnetic resonance imaging system 100. The computer storage 134 is further shown as containing a magnetic resonance fingerprinting dictionary 144. The computer storage is further shown as containing a magnetic resonance image 146 that was reconstructed using the magnetic resonance data 142 and the magnetic resonance fingerprinting dictionary 144.

The computer memory 136 contains a control module 150 which contains such code as operating system or other instructions which enables the processor 130 to control the operation and function of the magnetic resonance imaging system 100. The computer memory 136 is further shown as containing a magnetic resonance fingerprint dictionary generating module 152. The fingerprint generating module 152 may model one or more spins using the Bloch equation for each voxel to construct the magnetic resonance fingerprinting dictionary 144. The fingerprinting dictionary 144 may comprise a plurality of tissue parameter sets. Each tissue parameter set may be assigned with pre-calculated signal evolution data which comprises data of a plurality of pre-calculated signal evolution curves. Each of the pre-calculated signal evolution curves is assigned to one SSFP state of the multiple SSFP states and characterizes a signal evolution of the respective SSFP state due to a variation of acquisition parameters from acquisition step to acquisition step, e.g. a variation of the absolute value of the flip angle, the radiofrequency phase, the gradient field, the echo time, and/or the repetition time. The computer memory 136 is further shown as containing an image reconstruction module 154 that uses the magnetic resonance data 142 and the magnetic resonance fingerprinting dictionary 144 to reconstruct the magnetic resonance image 146. For reconstruction of the images 146, each voxel may be assigned with a set of tissue parameters. The respective tissue parameters may be identified determining the pre-calculated signal evolution data which best matches the acquired multiple SSFP state magnetic resonance data 142. In case each pre-calculated signal evolution data of each tissue parameter set comprises data of a plurality of pre-calculated signal evolution curves each calculated for a different SSFP state, for each tissue parameter set inner products may be determined between each normalized acquired signal evolution curve and the pre-calculated normalized signal evolution curve of the tissue parameter set which are assigned to the same SSFP state. The best average matching tissue parameter set, e.g. the tissue parameter for which the highest average inner product of the inner products of the individual curves is calculated, may be assigned to the respective voxel. Assigning a tissue parameter set to each voxel, a tissue parameter map may be reconstructed. This tissue parameter map may be used for reconstructing images 146 each illustrating one or more of the tissue parameters comprised of the assigned sets of for tissue parameters. For example, the magnetic resonance image 146 may be a rendering a two-dimensional slice through the subject 118.

The contents of the computer storage 134 and the computer memory 136 may duplicate each other or the contents of either may be exchanged.

Figure 2:
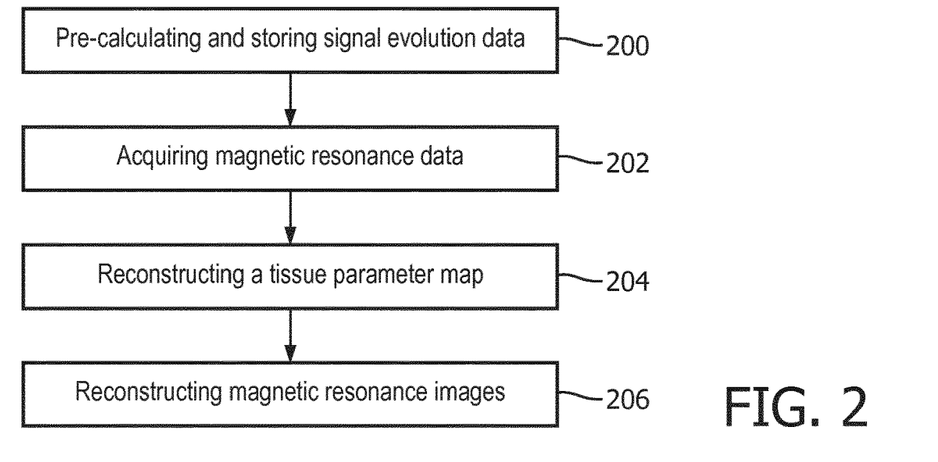
FIG. 2 shows a flow chart which illustrates a method of using the exemplary magnetic resonance imaging system of FIG. 1.

FIG. 2 shows a flowchart which illustrates an example of a method of operating the magnetic resonance imaging system 100 of FIG. 1. In block 200, for each tissue parameter set signal evolution data is pre-calculated. The pre-calculated signal evolution data of each tissue parameter set may comprise data of a plurality of pre-calculated signal evolution curves each calculated for a different SSFP state. In other words, for each tissue parameter set a plurality of pre-calculated signal evolution curves may be pre-calculated. Each of these pre-calculated signal evolution curves predicts a signal evolution for the respective tissue parameter and the respective SSFP state. When pre-calculating the pre-calculated signal evolution curves for each one of the multiple SSFP states the signal evolution data may be modeling using the tissue parameter and varying one or more of the following parameters: the absolute value of the flip angle, the radiofrequency phase, the gradient field, the echo time, and the repetition time.

In block 202, magnetic resonance data 142 of multiple SSFP states per repetition time is acquired according to magnetic resonance fingerprinting protocol. For example, magnetic resonance data 142 of the five central SSFP states $F_{-2}$, $F_{-1}$, $F_0$, $F_1$, and $F_2$ is acquired. For example, one or more of the following parameters are, e.g. pseudo-randomly, varied during the acquisition of the multiple SSFP state magnetic resonance data 142: an absolute value of a flip angle, a radiofrequency phase, a gradient field, an echo time, and the repetition time. Since magnetic resonance data 142 of different SSFP states may be acquired at different points of time during a repetition, the magnetic resonance data 142 of different SSFP states may be deinterleaved or disentangle, resulting in a multitude of acquired signal evolution curves, wherein each acquired signal evolution curves is assigned to one SSFP state of the multiple SSFP states.

In block 204, a tissue parameter map for the acquired multiple SSFP state magnetic resonance data 142 is reconstructed. For each voxel, a set of tissue parameters is identified, the pre-calculated signal evolution data of which best matches the acquired multiple SSFP state magnetic resonance data. In case each pre-calculated signal evolution data of each tissue parameter set comprises data of a plurality of pre-calculated signal evolution curves, each calculated for a different SSFP state, e.g. $F_{-2}$, $F_{-1}$, $F_0$, $F_1$, or $F_2$, the best matching pre-calculated signal evolution data may e.g. be determined using a weighted sum over inner products $$\bar{\theta} = \frac{1}{n}\sum_j w_j \theta_j.$$

Here, $w_i$ may be a weighting factor and $\theta_j$ the inner product of the normalized acquired signal evolution curve with the normalized pre-calculated signal evolution curve assigned to the same, i.e. j-th, SSFP state $F_j$. In order to improve the total SNR, higher-order SSFP states $F_i$ with $|i|>1$, like e.g. i=2, 3, 4, or higher, may be weighted with a smaller weighting factor such that their SNR contribution to the total SNR is reduced. The pre-calculated signal evolution data for which the highest weighted sum is calculated may be identified as the best matching pre-calculated signal evolution data. Thus, the voxel of the acquired multiple SSFP state magnetic resonance data 142 evaluated here, may be assigned the tissue parameters of the best matching pre-calculated signal evolution data. Thus, tissue parameters may be assigned to each voxel generating a tissue parameter map. Taking into account higher-order SSFP states may result in a higher encoding capability for T2. Hence, the required acquisition time for acquiring sufficient magnetic resonance data 142 may significantly be reduce.

In block 206, the reconstructed tissue parameter map is used to reconstruct one or more magnetic resonance images. The type of the reconstructed images may depend on the type of tissue parameters comprised by the tissue parameter map. For example, T1-weighted or T2-weighted images may be reconstructed. Furthermore, e.g. images of the relative spin density $M_0$ or $B_0$ may be reconstructed.

Figure 3:
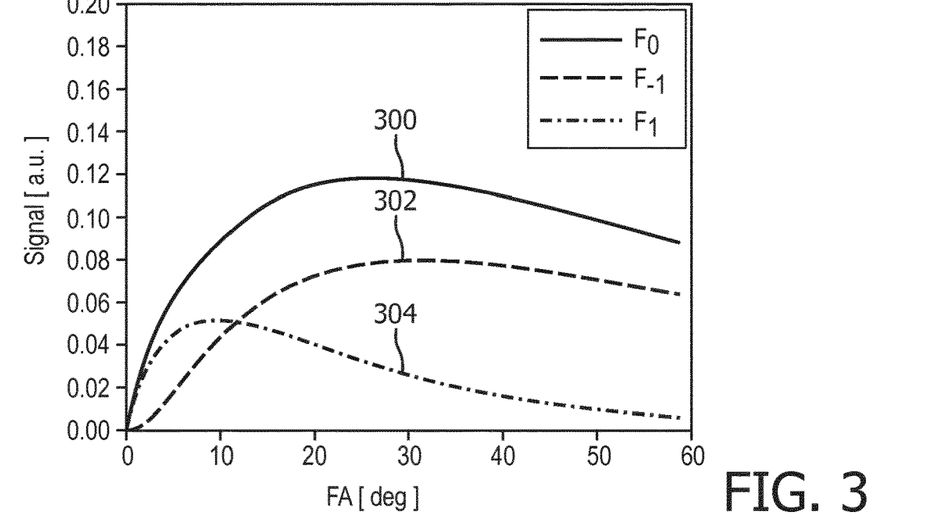
FIG. 3 illustrates exemplary simulated SSFP signals for typical tissue parameters.

FIG. 3 shows simulated SSFP signals for typical tissue parameters, i.e. T1=950 ms and T2=100 ms, as a function of flip angle for the three central SSFP states $F_{-1}$ 302, $F_0$ 300, $F_1$ 304. Each of the different SSFP states $F_{-1}$ 302, $F_0$ 300, $F_1$ 304 shows a unique dependence on the flip angle. Thus, by varying the flip angle unique signal evolutions curves 300, 302, 304 for each of the SSFP states may be acquired.

Figure 4A:
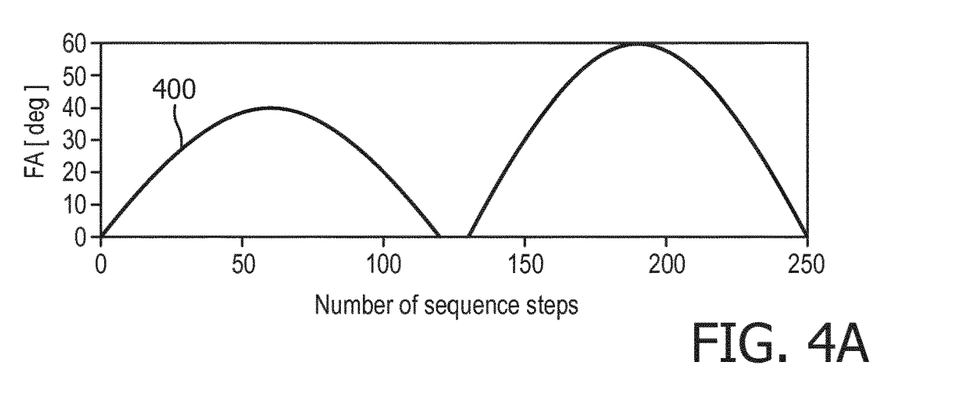
FIG. 4A to 4C illustrate the dependency of SSFP signal curves for typical tissue parameters using a fingerprinting protocol.

FIG. 4A shows an exemplary flip angle (FA) pattern 400 used for calculating the simulated signal evolution curves shown in FIG. 3B. In this example, a fixed repetition time of TR=15 ms was employed.

Figure 4B:
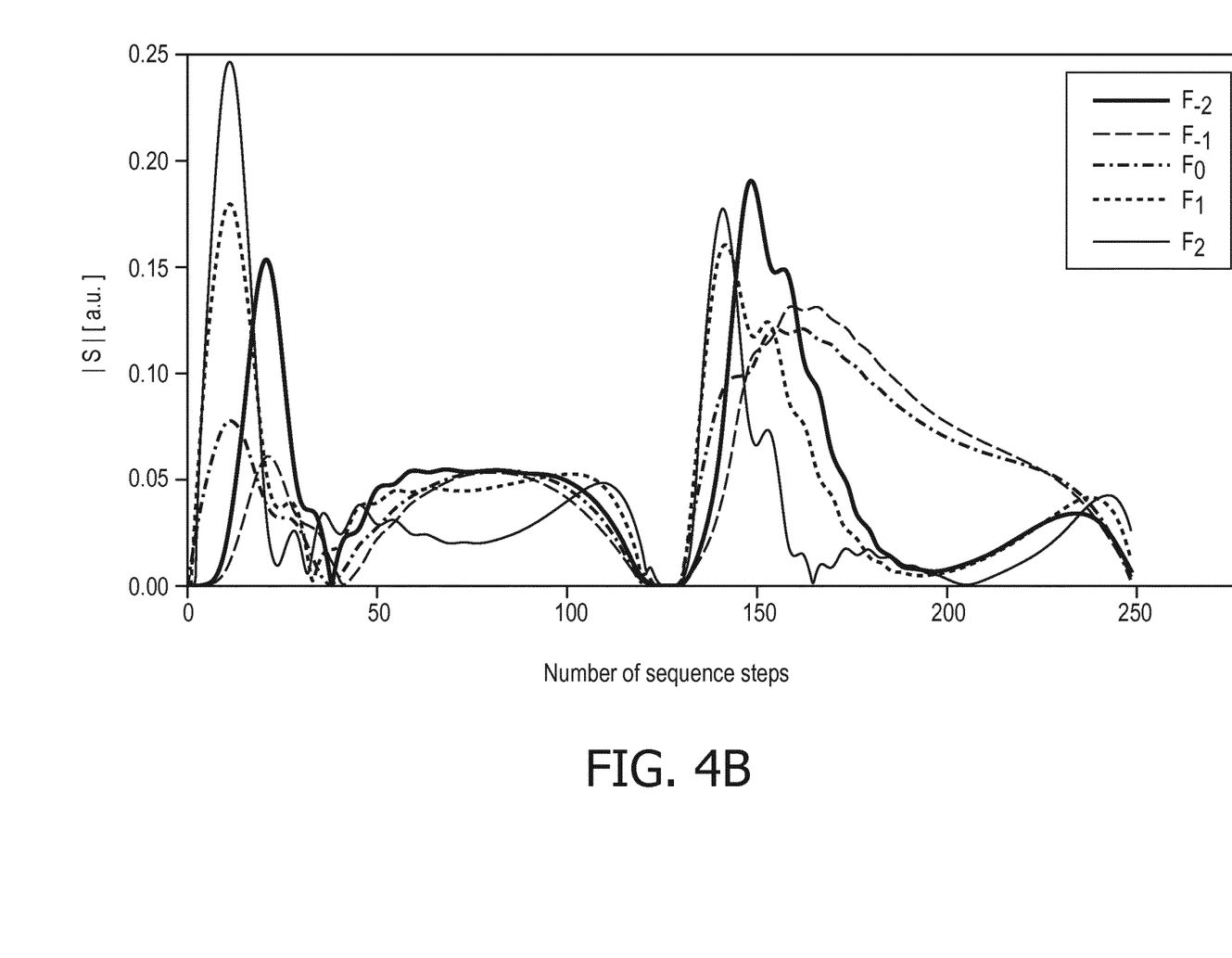

FIG. 4B shows exemplary simulated signal evolution curves for the FA pattern 400 of FIG. 4A. Depicted are the signals for the five central SSFP states $F_{-2}$, $F_{-1}$, $F_0$, $F_1$, and $F_2$ for typical tissue parameters, in this example T1=950 ms and T2=100 ms. Note that all signal curves are already normalized. The tissue parameters T1=950 ms and T2=100 ms represent a single tissue parameters set of the dictionary. From FIG. 4B, it becomes apparent that unique signal curves may be obtained for all five SSFP states $F_{-2}$, $F_{-1}$, $F_0$, $F_1$, and $F_2$.

Figure 4C:
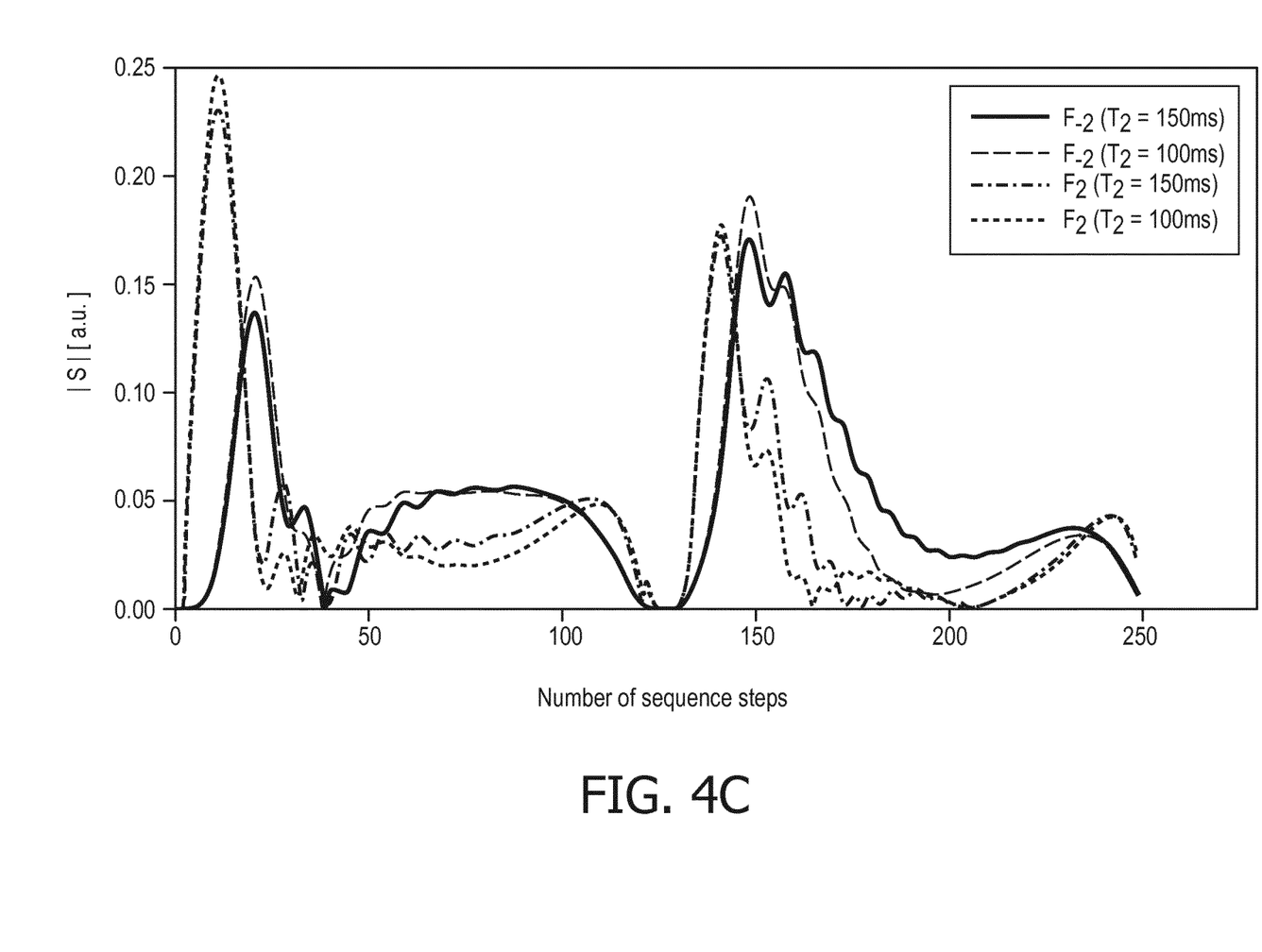

FIG. 4C shows exemplary simulated signal evolution curves of the SSFP states $F_2$ and $F_2$ for the FA pattern of FIG. 3 for T1=950 ms and two different T2 values, i.e. T2=100 ms and T2=150 ms. From FIG. 4C, the pronounced T2 dependence of the additionally acquired higher-order SSFP states, i.e. $F_2$ and $F_2$, becomes apparent. Taking into account these higher-order SSFP states $F_2$ and $F_2$ may thus result in a more efficient identification of a best matching tissue parameter set comprising T2 as a tissue parameter. Each tissue parameter set comprising a specific value of T2 may be assigned with pre-calculated signal evolution curves of the SSFP states $F_2$ and $F_2$ that differ considerably from pre-calculated signal evolution curves of the SSFP states $F_2$ and $F_2$ of other tissue parameter set comprising different values of T2. Thus, taking into account higher-order SSFP states may enable a more efficient differentiation of tissue parameter sets with different values of T2, i.e. provide a higher encoding capability for T2. Hence, the required acquisition time for acquiring sufficient magnetic resonance data 142 may significantly be reduce: The encoding capability of MRF sequences is usually much higher for T1 than T2. Consequently, the minimum length of variation patterns to be applied and therefore of the entire measurement, is mainly determined by the accuracy of the T2 estimates. However, with a higher encoding capability for T2, the required acquisition time may significantly be reduced.

Taking into account the higher-order SSFP states $F_2$ and $F_2$ may e.g. comprise acquiring magnetic resonance data 142 for each of these SSFP states $F_2$ and $F_2$ at each sequence step, i.e. during each repetition time. Identifying the best matching pre-calculated signal evolution data may comprise comparing the acquired signal evolution curves and pre-calculated signal evolution curves which are assigned to the SSFP states $F_2$ and $F_2$. The result of these comparisons, e.g. using inner products as described above, may facilitate the differentiation of tissue parameter sets with different values of T2 and thus accelerate as well as simplify the reconstruction of a tissue parameter map.

Figure 5:
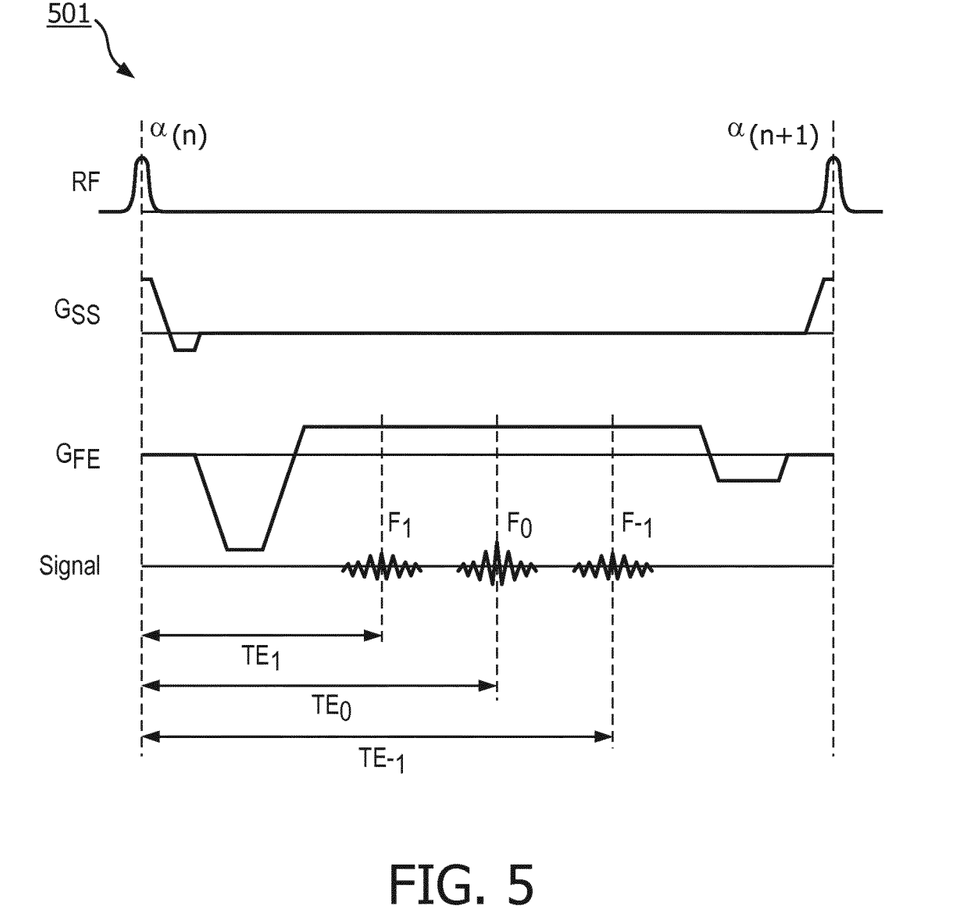
FIG. 5 diagrammatically shows an MR fingerprinting acquisition block that can be acquired with an MRI system according to embodiments of the invention.

FIG. 5 diagrammatically shows an MR fingerprinting acquisition block 501 that can be acquired with an MRI system according to embodiments of the invention. In the MR fingerprinting sequence the flip angle constantly varied, which is indicated by the $\alpha_n$ and $\alpha_{n+1}$. By means of this acquisition block three echos will be acquired corresponding to the F1, F0 and F-1 states or basis functions that describe the spin system after the previous RF pulse.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 measurement zone or imaging zone
110 magnetic field gradient coils
112 magnetic field gradient coil power supply
114 radio-frequency coil
116 transceiver
118 subject
120 subject support
122 actuator
126 computer system
128 hardware interface
130 processor
132 user interface
134 computer storage
136 computer memory 140 pulse sequence commands
142 magnetic resonance data
144 magnetic resonance fingerprinting dictionary
146 magnetic resonance image
150 control instructions
152 magnetic resonance fingerprint dictionary generating instructions
154 image reconstruction instructions
200 pre-calculating and storing signal evolution data
202 acquiring magnetic resonance data
204 reconstructing a tissue parameter map
206 reconstructing magnetic resonance images

The invention claimed is:

1. A magnetic resonance imaging system for acquiring magnetic resonance data from a subject within a measurement zone, wherein the magnetic resonance imaging system comprises:
a processor for controlling the magnetic resonance imaging system;
a memory storing machine executable instructions, pulse sequence commands and a dictionary, wherein the pulse sequence commands are configured for controlling the magnetic resonance imaging system to acquire magnetic resonance data of multiple steady state free precession (SSFP) states after execution of each pulse sequence command, wherein the pulse sequence commands are further configured for controlling the magnetic resonance imaging system to acquire the magnetic resonance data of the multiple SSFP states according to a magnetic resonance fingerprinting protocol, the dictionary comprising a plurality of tissue parameter sets, each tissue parameter set being assigned with signal evolution data pre-calculated for multiple SSFP states;
wherein execution of the machine executable instructions causes the processor to:
acquire the magnetic resonance data of the multiple SSFP states for a plurality of voxels by controlling the magnetic resonance imaging system with the pulse sequence commands according to the magnetic resonance fingerprinting protocol; and
reconstruct a tissue parameter map for the acquired multiple SSFP state magnetic resonance data, wherein the reconstruction comprises for each voxel identifying the pre-calculated signal evolution data provided by the dictionary which best matches the acquired multiple SSFP state magnetic resonance data and assigning the tissue parameter set of the best matching resonance pre-calculated signal evolution data to the respective voxel.

2. A magnetic resonance imaging system according to claim 1, wherein the pulse sequence commands are configured for controlling the magnetic resonance imaging system to acquire magnetic resonance data of multiple SSFP states per repetition time and wherein the processor is caused to acquire the magnetic resonance data of the multiple SSFP states per repetition time for a plurality of voxels by controlling the magnetic resonance imaging system with the pulse sequence commands according to the magnetic resonance fingerprinting protocol.

3. The magnetic resonance imaging system of claim 1, wherein for each of the tissue parameter sets the pre-calculated signal evolution data comprises data of a plurality of pre-calculated signal evolution curves, wherein each of the pre-calculated signal evolution curves is assigned to one SSFP state of the multiple SSFP states and characterizes a signal evolution of the respective SSFP state, wherein the acquired multiple SSFP state magnetic resonance data comprises data of a plurality of acquired signal evolution curves, wherein each of the acquired signal evolution curves is assigned to one SSFP state of the multiple SSFP states,
wherein the identification of the pre-calculated signal evolution data best matching the acquired multiple SSFP state magnetic resonance data comprises determining matching factors for each comparison of acquired signal evolution curves and pre-calculated signal evolution curves which are assigned to the same SSFP state and using the matching factors for identifying the best matching pre-calculated signal evolution data.

4. The magnetic resonance imaging system of claim 3, wherein the determining of matching factors further comprises calculating an average matching factor for the pre-calculated signal evolution data of each tissue parameter set and identifying the pre-calculated signal evolution data with the best average matching factor as being the pre-calculated signal evolution data best matching the acquired multiple SSFP state magnetic resonance data.

5. The magnetic resonance imaging system of claim 4, wherein the matching of the acquired multiple SSFP state magnetic resonance data with the pre-calculated signal evolution data comprises determining an inner product between the normalized acquired signal evolution curves and the normalized signal evolution curves which are assigned to the same SSFP state and
wherein the best average match is given by the highest average inner product of the inner products.

6. The magnetic resonance imaging system of claim 3, wherein the identification of the pre-calculated signal evolution data best matching the acquired multiple SSFP state magnetic resonance data further comprises weighting the results of the comparing of the acquired multiple SSFP state magnetic resonance data with the individual signal evolutions using weighting factors.

7. The magnetic resonance imaging system of claim 6, wherein the results of the comparing of signal evolution curves assigned to higher-order SSFP states are assigned with smaller weighting factors than the results of the comparing with signal evolutions assigned to lower SSFP states.

8. The magnetic resonance imaging system of any one of the preceding claims, wherein the acquired multiple SSFP state magnetic resonance data comprises magnetic resonance data of the following SSFP states: $F_{-2}$, $F_{-1}$, $F_0$, $F_1$, and $F_2$.

9. The magnetic resonance imaging system of claim 1, wherein the acquiring of the multiple SSFP state magnetic resonance data according to the magnetic resonance fingerprinting protocol comprises varying one or more of the following parameters during the acquisition of the multiple SSFP state magnetic resonance data: an absolute value of a flip angle, a radiofrequency phase, a gradient field, an echo time, and the repetition time.

10. The magnetic resonance imaging system of claim 9, wherein the parameters are varied independently using one or more pseudo-random patterns.

11. The magnetic resonance imaging system of claim 1, wherein execution of the machine executable instructions further causes the processor to pre-calculate the signal evolution data of the dictionary, wherein the signal evolution data for the multiple SSFP states is pre-calculated for each tissue parameter set of the dictionary, and to store the pre-calculated signal evolution data in the dictionary in the memory.

12. The magnetic resonance imaging system of claim 11, wherein the pre-calculation of the signal evolution data comprises modeling for each one of the multiple SSFP states signal evolution data using variations of one or more of the following parameters: the absolute value of the flip angle, the radiofrequency phase, the gradient field, the echo time, and the repetition time.

13. The magnetic resonance imaging system of claim 1, wherein one or more magnetic resonance images are reconstructed using the tissue parameter map.

14. A non-transitory computer readable medium comprising machine executable instructions for execution by a processor controlling a magnetic resonance imaging system to acquire magnetic resonance data from a subject within a measurement zone, wherein execution of the machine executable instructions causes the processor to:
  acquire magnetic resonance data of multiple steady state free precession (SSFP) states per repetition time for a plurality of voxels according to a magnetic resonance fingerprinting protocol by controlling the magnetic resonance imaging system with pulse sequence commands configured for controlling the magnetic resonance imaging system to acquire the magnetic resonance data of the multiple SSFP states after execution of each pulse sequence command according to the magnetic resonance fingerprinting protocol; and
  reconstruct a tissue parameter map for the acquired multiple SSFP state magnetic resonance data, wherein the reconstruction comprises for each voxel identifying pre-calculated signal evolution data provided by a dictionary which best matches the acquired multiple SSFP state magnetic resonance data and assigning the tissue parameter set of the best matching pre-calculated resonance signal evolution data to the respective voxel, wherein the dictionary comprises a plurality of tissue parameter sets, each tissue parameter set being assigned with signal evolution data pre-calculated for multiple SSFP states.

15. A method of operating a magnetic resonance imaging system for acquiring magnetic resonance data from a subject within a measurement zone, wherein the method comprises:
  acquiring magnetic resonance data of multiple steady state free precession (SSFP) states for a plurality of voxels according to a magnetic resonance fingerprinting protocol by controlling the magnetic resonance imaging system with pulse sequence commands configured for controlling the magnetic resonance imaging system to acquire the magnetic resonance data of the multiple SSFP states after execution of each pulse sequence command according to the magnetic resonance fingerprinting protocol; and
  reconstructing a tissue parameter map for the acquired multiple SSFP state magnetic resonance data, wherein the reconstruction comprises for each voxel identifying pre-calculated signal evolution data provided by dictionary which best matches the acquired multiple SSFP state magnetic resonance data and assigning the tissue parameter set of the best matching resonance signal pre-calculated evolution data to the respective voxel, wherein the dictionary comprises a plurality of tissue parameter sets, each tissue parameter set being assigned with signal evolution data pre-calculated for multiple SSFP states.

* * * * *